United States Patent [19]

Helioff et al.

[11] Patent Number: 5,034,220

[45] Date of Patent: Jul. 23, 1991

[54] NON-AEROSOL SHAVING GEL

[75] Inventors: Michael W. Helioff, Westfield; Mohammed Tazi, Wayne; Robert B. Login, Oakland; John F. Tancredi, Kinnelon; Stephen L. Kopolow, Plainsboro; William J. Burlant, Wayne, all of N.J.

[73] Assignee: GAF Chemicals Corporation, Wayne, N.J.

[21] Appl. No.: 540,990

[22] Filed: Jun. 20, 1990

[51] Int. Cl.$^5$ .................................................. A61K A/15
[52] U.S. Cl. .......................................... 424/73; 424/45; 514/557; 514/772
[58] Field of Search .................. 424/45, 73; 514/557, 514/772; 434/73

[56] References Cited

U.S. PATENT DOCUMENTS

| 4,495,169 | 1/1985 | Schmolka | 424/45 |
| 4,744,979 | 5/1988 | Osipow | 424/73 |
| 4,775,530 | 10/1988 | Perricone | 514/557 |
| 4,944,939 | 7/1990 | Moore | 434/73 |
| 4,957,732 | 9/1990 | Grollier | 514/772 |

FOREIGN PATENT DOCUMENTS 0259843 8/1987 European Pat. Off. .
2166150 10/1984 United Kingdom .
2167429 11/1984 United Kingdom .

Primary Examiner—Thurman K. Page
Assistant Examiner—William E. Benston, Jr.
Attorney, Agent, or Firm—Walter Katz; Marilyn J. Maue; Joshua J. Ward

[57] ABSTRACT

A non-aerosol shaving gel of the invention consists essentially of a major amount of a resin gel-former which is a crosslinked, neutralized copolymer of maleic anhydride and a $C_1$-$C_5$ alkyl vinyl ether, a water-soluble soap and water.

16 Claims, No Drawings

NON-AEROSOL SHAVING GEL

BACKGROUND OF THE INVENTION

1. Field of the Invention

This invention relates to non-aerosol shaving gels, and, more particularly, to such shaving preparations which have advantageous properties during use.

2. Description of the Prior Art

U.S. Pat. No. 3,541,581 describes a post-foaming aerosol gel as a shaving preparation which consisted of an aqueous dispersion of a soap, a water-soluble gelling aid, and a post-foaming agent having a high vapor pressure at room temperature. The product was discharged from an aerosol container as a stable gel and the foam was developed in situ on the surface of the skin by vaporization of the low boiling point agent.

U.S. Pat. No. 3,314,857 describes a transparent shaving cream with good lubricating properties which deposited a skin protective layer and which did not emulsify the natural skin oils. The composition included a polydimethyl siloxane, a crosslinked, water-soluble polyacrylic acid, triethanolamine, and a non-ionic surfactant.

U.S. Pat. No. 4,046,874 describes a shaving cream adapted for dry shaving using a conventional razor blade comprising an aqueous foam containing in the aqueous phase a polyglycerol ester such as triglycerol monostearate and a texturizing amount of a water-insoluble pulverulent bodying agent such as sodium silicoaluminate.

These and other shaving soaps, creams, and aerosol foams, however, do very little in the way of acting as lubricants to assist the process of shaving. In addition, because they may contain ionic emulsifiers, they can emulsify protective skin oils, leaving the skin dry, unprotected and subject to irritation from the emulsifiers, the scraping action of the razor blade, and from sun, wind and perspiration.

For these reasons, present day shaving preparations do not address the special problems of the black-skinned male in removing facial hair. Since the facial hair of the black male is often curly and wiry, shaving such hairs leaves the exposed ends with sharp points and as the hairs regrow these sharp points can actually turn back onto and penetrate the skin, causing a clinical condition called "pseudofolliculitis barbae". For this reason, many black men do not shave but prefer to use a depilatory which can give a close "shave" and leave the hair tip soft and blunt so that it will not puncture and re-enter the skin.

An object of the present invention, therefore, is to provide a non-aerosol shaving gel formulation which can provide effective razor glide, lubricity, creaminess and which leaves a protective film on the skin of the user.

Another object herein is to provide a hydrophobic crosslinked, neutralized maleic anhydride-$C_1$-$C_5$ alkyl vinyl ether copolymer, water-soluble soap in a gel composition for use as a non-aerosol shaving preparation.

Still another object herein is to provide a non-aerosol shaving gel composition which is particularly useful for sensitive skin which are characterized by a plurality of small bumps over its entire surface such as is frequently encountered by black males.

These together with other objects and advantages will become apparent from the following description.

SUMMARY OF THE INVENTION

The non-aerosol shaving gel formulation of the invention consists essentially of a major amount of a resin gel-former which is a crosslinked, neutralized maleic anhydride-$C_1$-$C_5$ alkyl vinyl ether copolymer, a water-soluble soap and water. Other ingredients are advantageously included in the formulation. Accordingly, the essential and preferred components of the composition of the invention includes the following:

ESSENTIAL COMPONENTS (1) a resin gel-former, i.e. a water-soluble salt of a crosslinked, neutralized Gantrez ® copolymer;
(2) a soap, i.e. a water-soluble salt of a high molecular weight fatty acid; and
(3) a large amount of water.

PREFERRED COMPONENTS (1) a lubricant, preferably a polyvinylpyrrolidone (PVP)-silicone composite; and
(2) miscellaneous additives such as humectants, emulsifiers, preservatives, skin conditioners, surfactants, and/or fragrances.

The non-aerosol shaving gel formulation of the invention provides the following features for the user:
(1) it will deposit a protective layer to enhance the natural action of skin oils;
(2) it will not emulsify protective skin oils unduly and thereby it will assist shaving without skin irritation or drying;
(3) it will contribute superior lubricity during use to minimize razor drag and skin irritation; and
(4) it can be used effectively by black males and others having a substantial number of bumps on their facial skin areas.

DETAILED DESCRIPTION OF INVENTION

1. COMPOSITION OF INVENTION

|  | Percent by Weight | | |
| --- | --- | --- | --- |
|  | Suitable | Preferred | Optimum |
| A. Essential Components | | | |
| 1. Crosslinked, neutralized Gantrez ® copolymer | 0.2–5 | 0.5–1.5 | 0.8 |
| 2. Water-soluble Soap | 3–15 | 5–10 | 8 |
| 3. Water | 80–96.8 | 88.5–94.5 | 91.2 |
| B. Preferred Components | | | |
| 1. Lubricant | 0–50 | 10–30 | 20 |
| 2. Humectant | 0–34 | 9–25 | 16.6 |
| 3. Emulsifier | 0–5 | 0.5–2 | 1 |
| 4. Preservative | 0–4 | 0.8–2 | 1 |
| 5. Surfactant | 0–10 | 3–8 | 5 |
| 6. Fragrance | 0–1 | 0.2–0.6 | 0.4 |

When one or more of the preferred components are present in the composition, the amount of water therein is reduced accordingly.

2. DESCRIPTION OF COMPONENTS OF COMPOSITION

Essential Components

A-1 - Crosslinked, Neutralized Gantrez ® Copolymer

The crosslinked, neutralized Gantrez ® copolymer component of the composition of the invention is a maleic anhydride-$C_1$-$C_5$ alkyl vinyl ether copolymer neutralized with sodium hydroxide or potassium hydroxide. A preferred crosslinked Gantrez ® is a copolymer of maleic anhydride and methyl vinyl ether crosslinked with about 1 to about 5 mole percent based on the monovinyl alkyl ether of a crosslinking agent. Suitable crosslinking agents include 1,9-decadiene, 1,7-octadiene, divinyl benzene, the divinyl ethers of an aliphatic diol acrylamides, acrylates and the like. Upon neutralization, such crosslinked copolymers provide gels of high viscosities and excellent stability.

The crosslinked, neutralized Gantrez ® component suitably comprises about 0.2-5% by weight of the composition. Low percentages provide a relatively thin composition while high percentages will produce a relatively thick gel.

The crosslinked, neutralized Gantrez ® component in the composition provides the resinous structure of the gel and forms a film on the skin both before and during shaving.

A-2 - Water-Soluble Soap

The soap component is a water-soluble salt of a higher fatty acid, i.e. $C_{10}$-$C_{24}$ fatty acids. Soaps are well known in the art and may be prepared in any conventional manner. For example, soaps may be prepared by reacting a basic material such as triethanolamine directly with a higher fatty acid such as stearic, palmitic, myristic, oleic, coconut oil fatty acids, soya oil fatty acids, and mixtures of these acids.

The nature of the soap used, although not critical, has an effect on the type of gel produced. Preferred soaps include the water-soluble stearate and palmitate soaps, such as the potassium, ammonium, and soluble amine soaps of commercial stearic acid and palmitic acid. The triethanolamine and morpholine soaps of these acids are preferred. The product sold commercially as stearic acid is actually a mixture consisting primarily of stearic and palmitic acids. The term "stearates" is used herein to designate soaps of commercial stearic acid, although soaps of chemically pure stearic acid would be the equivalent for the purposes of this invention. The soaps may be made by neutralization of the appropriate higher fatty acid with suitable alkali, or may be introduced in the form of animal fats, such as tallow, or vegetable fats, such as palm oil, which are rich in the appropriate acid and which, when saponified, form soaps rich in the corresponding acid.

The amount of soap employed to form the gel generally depends upon the nature of the soap used. The low limit is the minimum amount which gives a satisfactory gel, and the upper limit is fixed either by economic considerations or by the amount which will form a suitable gel as the highest temperatures likely to be encountered in use. The beneficial effects of the instant invention are achieved to an optimum degree when the composition contains an appreciable amount of soap, such as specified within the preferred range.

The function of the soap in the composition of the invention is to fill up the pores of the resinous structure of the gel provided by the crosslinked Gantrez ®. In addition, soap aids the wetting characteristics of the preparations described.

A-3 - Water

The water in the composition of the present invention is requisite for the preparation of a suitable gel having desirable shaving properties. It has been found that water (tap water, distilled water, deionized water, etc.) possesses adequate solubility for the soap and has the required compatibility with the resin to produce stable gels of the invention. In general, relatively small amounts of polar substances, such as lower molecular weight alcohols, methanol, ethanol, propanol, isopropanol, and the like may be used; the only requirement being that sufficient water be present to maintain the desired physical characteristic of the gel. Generally, the amount of water employed in the gel may be varied depending upon the properties desired in the final product. The amount of water employed depends on the nature of the soap and resin used.

It has been found, however, that at least about 80 percent and preferably from about 80 to about 95 percent by weight of the total gel composition should be water although higher amounts may be employed if desired, e.g., up to about 97 percent by weight of the total composition. The upper limit is the maximum amount that produces a satisfactory gel at the temperatures likely to be encountered in use, while the lower limit is fixed substantially by economic considerations.

Preferred Components

B-1 - Lubricant

The lubricant in the composition of the invention contributes to the comfort, closeness and speed of wet shaving. It is known in the art to use polysiloxanes and polysilicone fluids for their lubricating properties and these may be included in the composition of the invention for this purpose. Mineral oils, lanolin or isopropyl myristate also can be included to supplement the effects of the free fatty acid. Water-soluble polymers such as polyvinylpyrrolidone, sodium carboxymethyl cellulose or polyacrylic acid and its derivatives, can also improve lubrication and/or skin irritation caused by other compounds.

However, a preferred lubricant for use herein is disclosed in copending U.S. patent application, Ser. No. 510,017, filed Apr. 17, 1990, the entire disclosed of which is incorporated by reference herein. This lubricant composition includes individual droplets of a non-volatile silicone fluid encapsulated within a thin film of polyvinylpyrrolidone. These discrete droplets of encapsulated silicone fluid can be maintained as a stable dispersion or as a separate layer in an aqueous medium by controlling the viscosity of the solution. This composition is prepared by dispersing the non-volatile silicone fluid in an aqueous medium containing a vinylpyrrolidone monomers optionally including other monomers to be copolymerized therewith, and polymerizing the vinylpyrrolidone monomer in situ while maintaining the integrity of the silicone fluid dispersion. This results in the formation of a thin film (shell) of polyvinylpyrrolidone surrounding the individual dispersed particles of the silicone fluid (core).

Suitable non-volatile silicone fluids used in making these stabilized droplets may be either a polyalkyl siloxane, a polyaryl siloxane, a polyalkylaryl siloxane or a polyether siloxane copolymer, which are present at a level of from about 1.0% to about 18%. Preferably, the silicone fluid is present in an amount from about 2.0% to about 8.0%. Mixtures of silicone fluids also may be used so long as the final mixture is non-volatile. The dispersed silicone particles should also be insoluble in the medium. As used herein, the word "insoluble" means that it does not substantially dissolve in water and is essentially immiscible therewith.

Non-volatile polyalkylsiloxanes that may be used include, for example, polydimethylsiloxane with viscosities ranging from about 5–600,000 centistokes at 25° C.

The siloxanes are available, for example, from the General Electric Company as the VISCASIL series and from Dow Corning as the Dow Corning 200 series. The viscosity can be measured by means of a glass capillary viscometer as set forth in Dow Corning Corporate Test Method CTM 0004 of July 20, 1970. Preferably, the viscosity ranges from about 350 centistokes to about 100,000 centistokes.

Non-volatile polyalkylarylsiloxanes that may be used include, for example, polymethylphenylsiloxanes having viscosities of from about 15–65 centistokes at 25° C. These siloxanes are available, for example, from the General Electric Company as SF 1075 methylphenyl fluid or from Dow Corning as 556 Cosmetic Grade Fluid. Additionally, poly(dimethylsiloxane)(diphenylsiloxane) copolymers having a viscosity in the range of from about 10–100,000 centistokes at 25° C. are useful.

Non-volatile polyethersiloxane copolymers suitable for use in the invention include, for example, a polypropylene oxide modified dimethylpolysiloxane, e.g., Dow Corning DC-1248, although ethylene oxide or mixtures of ethylene oxide and propylene oxide may also be used.

Suitable silicones are disclosed in U.S. Pat. No. 2,826,551, 3,964,500, 4,364,837, and British Patent No. 849,433 to Woolston. The disclosures of these patents are incorporated herein by reference. In addition, the disclosure Silicone Compounds distributed by Petrarch Systems Inc., 1984, is incorporated by reference. This literature provides an extensive listing of suitable silicone materials.

To prepare these stabilized silicone fluid droplets, the silicone fluid is added to water and subjected to agitation or high speed dispersion so as to produce a fine dispersion of discrete silicone fluid droplets throughout the aqueous medium.

Thereafter, a vinylpyrrolidone monomer is added to the mixture, along with an appropriate initiator. If desired, an additional monomer for purposes of forming a copolymer may be added. Typical co-monomers include dimethylaminopropyl methacrylate, dimethylaminoethyl methacrylate, methacrylamidopropyltrimethylammonium chloride, acrylamide, and neutralized acrylic acid.

In addition, a suitable polymerization catalyst for vinylpyrrolidone is then added. Typical of these catalysts are t-butylperoctoate, t-butylperoxypivalate, and the like. Conventional catalysts for the polymerization of vinyl pyrrolidone are suitable.

Thereafter, the polymerization is carried out by maintaining the reaction mixture at a temperature in the range from about 55° to 85° C., preferably, from about 75° to 85° C., and most preferably, from about 78° to 82° C., for a period of time sufficient to produce the desired effect of providing a film about the discrete droplets of silicone fluid.

In a similar manner, as the viscosity of the solution of the medium is decreased by decreasing the amount of vinylpyrrolidone monomer in the initial mixture which results in a more dilute concentration of vinylpyrrolidone polymer in the ultimate mixture, the proclivity to form a separate layer of the discrete silicone fluid droplets is enhanced.

Generally, the amount of monomer to silicone fluid is in the range from about 95/5 to 5/95 on a weight basis. We have found that as the ratio becomes less than about 50/50, the production of a stable suspension is significantly decreased. As used herein, a "stable suspension" means that the discrete droplets of the silicone fluid remain suspended on standing for seven days at ambient temperature.

In order to produce a stable suspension, the amount of vinylpyrrolidone monomer to silicone fluid is preferably in the range from about 95/5 to 60/40. Most preferred is the range from about 90/10 to 80/20.

When the particle size of the dispersed droplets are in the range from about 45 to 450$\mu$, a viscosity of about 12,000 cps is suitable to maintain a stable suspension. When the particle size of the droplets are in the range from about 10 to 100$\mu$, stability can be obtained at a viscosity of approximately 6,000 cps.

Accordingly, a dispersion of a silicone fluid (Dimethicone) was prepared by adding 10 grams of Dimethicone having a viscosity of 100 cs to a reactor kettle in 400 grams of distilled water. The mixture was stirred at 300 to 400 rpm to disperse the Dimethicone into discrete small droplets. The system was purged with nitrogen for 30 minutes.

The mixture was then heated to 80° C. and 0.25 grams of t-butylperoctoate was added. This temperature was maintained for 30 minutes with continuous stirring of the mixture.

Thereafter, 90 grams of vinylpyrrolidone were added at one time and an additional 0.25 grams of t-butylperoctoate was added. The mixture was maintained at 80° C. for 6 to 8 hours with continuous stirring. The vinylpyrrolidone residual content was monitored and it was considered that the reaction was complete when residual content was less than 0.1%.

The product obtained was a dispersion of minute droplets of the silicone fluid which remained suspended in the medium as a 90%-10% PVP:silicone composite containing 20% solids, i.e. 20 g. composite in 80 g. of water.

B-2 - Humectant

Up to about 28% of a humectant is included in the composition to prevent premature drying out of the gel. The humectant also has the effect of making the gel softer.

Suitable humectants include polyols such as sorbitol, glycerol, propylene glycol, dipropylene glycol, 1,3-butylene glycol. Preferably a combination of up to about 28% by weight of sorbitol and up to about 8% by weight of propylene glycol is used in the composition of the invention.

B-3 - Emulsifier

The emulsifier or non-ionic surfactants that are useful for the purposes of the present invention are of the polyoxyethylene derivative type and are generally used in an amount equal to not more than 10% by weight of the composition.

Of special utility are ethers formed from long chain fatty alcohols and alkylene oxides. Typical of these are commercially available products sold under the designation Brij 30 and Brij 35 which are ethers formed by condensing lauryl alcohol with ethylene oxide. Brij 30 is a liquid, oily product identified as polyoxyethylene (4) lauryl ether. Brij 35, on the other hand, is a waxy, solid product designated as polyoxyethylene (23) lauryl ether. The numbers in parentheses indicate the number of oxyethylene groups in each polyether.

B-4 - Preservative

Any suitable preservative may be used in the composition of the invention. A preferred preservative is Germaben ® sold by the Sutton Labs Div. of GAF Corporation, which is a mixture of diazolidinyl urea, methyl and propyl paraben, and propylene glycol.

B-5 - Surfactant

Certain surface active agents, usually called wetting agents, or surfactants, may also be used as the soap ingredient. The wetting agents so employed preferably are anionic or non-ionic in character. They should be appreciably soluble in the aqueous components of the gel and of the type that produce foam in water solution. Examples of such agents are triethanolamine lauryl sulfate, sodium lauryl sulfate, sodium dodecyl benzene sulfonate, water-soluble polyoxyethylene ethers of alkyl-substituted phenols, and water-soluble polyoxyethylene cetyl ethers,. Numerous anionic and nonionic wetting agents suitable for the purposes of the present invention are described in detail in McCutcheon's "Emulsifiers & Detergents Annual," 1967. Although not essential to the invention, in some cases it may be desirable to add minor concentrations of a wetting agent to the gel as a supplement to the water-soluble soaps described above. the wetting agent has been found to be effective in removing oily residue from the skin and in facilitating rinsing the lather from the skin. When thus added to the composition as a soap supplement, the surfactant or wetting agent should be used in minor concentrations, preferably from about 3.0 percent to about 8 percent by weight of the gel.

A preferred surfactant is a non-ionic surfactant, such as Igepal ® CO-630 (9 mole ethylene oxide), which is a preferred component in the composition of the invention.

COMPOSITION OF INVENTION

| Components | % by Weight |
|---|---|
| A-1. Crosslinked Gantrez ® (GAF) | 0.8 |
| Sodium Hydroxide, 10% | 2.5 |
| 2. Palmitic Acid | 5.8 |
| Stearic Acid, T.P. | 2.0 |
| Triethanolamine, 98% | 4.2 |
| 3. Deionized Water | 44.3 |
| B-1. PVP-4 Silicone Composite, 90/10, 20% solids | 20.0 |
| 2. a. Sorbitol, 70% | 10.0 |
| b. Propylene glycol | 3.0 |
| 3. Brij 58 | 1.0 |
| 4. Germaben, II-E | 1.0 |
| 5. Igepal CO-630 | 5.0 |
| 6. Fragrance | 0.4 |
| | 100.0 |

The composition is prepared by adding A-1 in A-3 to A-2, heating to 60°-70° C. for 5-10 minutes, cooling to 35°-40° C. with constant mixing, and then adding B-1 to B-6.

NOTES

A-1 is a polyvinylmethylether-maleic anhydride copolymer.
B-1 is prepared according to the example above.
B-4 is a methylparaben-propylparaben.
B-5 is a nonoxynol.

When the composition above is used as a shaving preparation it is found that it provides a protective film on the skin which promotes effective razor glide, superior lubricity and a non-irritating feel on the skin, creaminess, and body, in a non-aerosol shaving gel which is convenient to use.

What is claimed is:

1. A non-aerosol shaving gel composition consisting essentially of about 0.2–5% by weight of a crosslinked, neutralized maleic anhydride-$C_1$-$C_5$ alkyl vinyl ether copolymer, about 3–15% by wt. of a soap component which is a water-soluble salt of a higher fatty acid $C_{10}$-$C_{24}$ water-soluble soap, and about 80–97% by weight of water.

2. A non-aerosol shaving gel composition according to claim 1 which consists essentially of about 0.5–1.5% by weight of said copolymer, about 5–10% by weight of said soap, and about 88–95% by weight of water.

3. A non-aerosol shaving gel composition according to claim 1 which consists essentially of about 0.8% by weight of said copolymer, about 8% by weight of said soap, and about 91.2% by weight of water.

4. A non-aerosol shaving gel composition consisting essentially of about 0.2–5% by weight of a crosslinked, neutralized maleic anhydride-$C_1$-$C_5$ alkyl vinyl copolymer, about 3–15% by weight of a water-soluble soap, one or more of the following: a lubricant, a humectant, an emulsifier, a preservative, a surfactant and a fragrance, the remainder being water.

5. A non-aerosol shaving gel composition according to claim 4 which includes about 10–30% by weight of a PVP-silicone composite lubricant, about 9–25% by weight of a humectant, about 0.5–2% by weight of an emulsifier, about 0.8–2% by weight of a preservative, and about 3–8% by weight of a surfactant.

6. A non-aerosol shaving gel composition according to claim 5 consisting essentially of about 0.8% by weight of a crosslinked, neutralized maleic anhydride-$C_1$-$C_5$ alkyl vinyl ether copolymer, and about 8% by weight of a water-soluble soap.

7. A non-aerosol shaving gel composition according to claim 5 wherein said copolymer is neutralized with sodium or potassium hydroxide, said soap is a water-soluble salt of a fatty acid, said PVP-silicone composite lubricant is a stable suspension of in situ polymerized vinyl pyrrolidone monomer in the presence of silicone fluid.

8. A non-aerosol shaving gel composition according to claim 7 wherein said silicone fluid is dimethyl siloxane polymers.

9. A non-aerosol shaving gel composition consisting essentially of about 0.5–15% by weight of a crosslinked, neutralized maleic anhydride-$C_1$-$C_5$ alkyl vinyl ether copolymer, about 5–10% by weight of a soap component which is a water-soluble salt of a higher fatty acid $C_{10}$-$C_{24}$ water-soluble soap, about 10–30% by weight of a lubricant, about 9–25% by weight of a humectant, about 0.5–2% by weight of an emulsifier, about 0.8–2% by weight of a preservative, about 3–8% by weight of a surfactant, the rest being water.

10. A non-aerosol shaving gel composition according to claim 9 which includes about 0.2–0.6% by weight of a fragrance.

11. A non-aerosol shaving gel composition according to claim 9 wherein said lubricant is a PVP-silicone composite 12. A non-aerosol shaving gel composition according to claim 9 wherein said soap is a mixture of palmitic and stearic acids.

13. A non-aerosol shaving gel composition according to claim 9 wherein said humectant is a mixture of sorbitol and propylene glycol.

14. A non-aerosol shaving gel composition according to claim 9 wherein said surfactant is a non-ionic surfactant.

15. A non-aerosol shaving gel composition according to claim 14 wherein said non-ionic surfactant is nonoxynol.

16. A non-aerosol shaving gel composition consisting essentially of about 0.8% by weight of a crosslinked, maleic anhydride-$C_1$-$C_5$ alkyl vinyl ether, about 2.5% by weight of 10% sodium hydroxide, about 5.8% by weight of palmitic acid, about 2.0% by weight of stearic acid, about 4.2% by weight of 98% triethanolamine, about 20% by weight of a 90% PVP-10% silicone composite, 20% solids, about 10% by weight of 70% sorbitol, about 3.0% by weight of propylene glycol, about 1.0% by weight of polyethylene glycol ether of cetyl alcohol about 1.0% by weight of a mixture of diazolidinyl urea, methyl and propylparaben and propylene glycol about 5.0% by weight of ethoxylated alkylphenol with 9 moles of ethylene oxide about 0.4% by weight of a fragrance, and 44.3% by weight of water.

* * * * *